United States Patent [19]

Kolesnik et al.

[11] 4,419,341

[45] Dec. 6, 1983

[54] DRUG FOR TREATMENT OF DENTAL CARIES

[75] Inventors: Anatoly G. Kolesnik, Moscow; Galina I. Kadnikova, Riga; Lilia V. Morozova, Moscow; Lidia M. Boginskaya, Moskovskaya, all of U.S.S.R.

[73] Assignee: Rizhsky Meditsinsky Institut, Moscow, U.S.S.R.

[21] Appl. No.: 472,085

[22] Filed: Mar. 4, 1983

[51] Int. Cl.$^3$ .................. A61K 7/18; A61K 33/16; A61K 35/32

[52] U.S. Cl. .................................... 424/52; 424/49; 424/57; 424/95; 424/151

[58] Field of Search .................................. 424/49–58, 424/95, 151

[56] References Cited

U.S. PATENT DOCUMENTS

| | | | |
|---|---|---|---|
| 1,664,182 | 3/1928 | Parisl | 424/95 |
| 2,154,168 | 4/1939 | Klein et al. | 424/57 |
| 2,182,171 | 12/1939 | Coyner | 424/95 |
| 2,968,593 | 1/1961 | Rapkin | 424/95 |
| 3,312,594 | 4/1967 | Cyr et al. | 424/151 |
| 3,431,339 | 3/1969 | Gyarmathy et al. | 424/52 |
| 3,743,721 | 7/1973 | Mattox | 424/95 |
| 3,932,606 | 1/1976 | Barth et al. | 424/52 |
| 4,157,386 | 6/1979 | La Rochelle | 424/52 |
| 4,169,885 | 10/1979 | Raaf et al. | 424/151 |
| 4,172,128 | 10/1979 | Thiele et al. | 424/95 |

FOREIGN PATENT DOCUMENTS 674909 7/1952 United Kingdom .................. 424/95

OTHER PUBLICATIONS

British Pharmacopoeia 1973, London, 1973, p. 431, Arzneimittel-Verzeichnis 1982, Teil I, Berlin, 1981, S, 76.

*Primary Examiner*—Shep K. Rose
*Attorney, Agent, or Firm*—Burgess, Ryan & Wayne

[57] ABSTRACT

A drug for treatment of dental caries, comprising an active principle, namely, a mixture of sodium monofluorophosphate and an anticarious preparation obtained by treating osseous tissue with a diluted mineral acid till a complete dissolution of mineral components and water-soluble proteins contained in the osseous tissue, separating the solution, diluting it with water, adding a stabilizer, i.e., citric acid or its salt, to the solution, and neutralizing and evaporating the solution, which anticarious preparation has the following percentage-by-weight composition:

| | |
|---|---|
| calcium | 2–6 |
| sodium | 19–23 |
| potassium | 0.04–0.18 |
| mineral acid anions | 6–10.6 |
| orthophosphoric acid anions | 1.5–5.0 |
| water-soluble proteins | 1.0–5.0 |
| magnesium | 0.05–0.2 |
| trace elements, including fluorine, manganese, tin, zinc, and iron | 0.01–0.02 |
| complex citrate compounds in terms of citric acid anions | the balance; | and a pharmaceutical diluent, the ratio between said active principle and said diluent being 1:23.5–24.5.

3 Claims, No Drawings

DRUG FOR TREATMENT OF DENTAL CARIES

The present invention relates to stomatology and is more specifically concerned with a drug for treatment of dental caries. The drug according to the invention is intended for per os administration and can be used for preventive and therapeutical treatment of dental caries.

BACKGROUND OF THE INVENTION

There are known different tabletted drugs for preventive and therapeutical treatment of dental caries, in which the active principle is sodium fluoride (cf. Farmacopeia romana, 1972, p. 460; British Pharmacopeia, 1973, p. 431).

There is further known a tabletted anticarious drug Calcipot-F (cf. Arzneimittel-Verzeichnis 1982, Teil 1, Berlin, 1981, S, 76), wherein the active principle comprises calcium and fluorine compounds. The composition, in grams, of this drug is as follows:

| | |
|---|---|
| $CaHPO_4$ | 0.29 |
| calcium citrate | 0.05 |
| calcium lactate | 0.01 |
| saccharose | 0.50 |
| lactose | 0.047 |
| magnesium silicofluoride | 0.0024 |

The total weight of one tablet is 1 g.

The overall anticarious effect of this drug is limited. This is manifest in a low concentration of fluorine, calcium and phosphorus ions in the saliva, a limited increase in the resistance of hard and soft tissues, and a limited decrease in the cariesogenic action of the dental deposit.

SUMMARY OF THE INVENTION

It is the principal object of the present invention to provide an effective anticarious drug which would raise the resistance to caries of hard and soft tissues in the oral cavity.

It is another object of the invention to provide a drug which would suppress the cariesogenic activity of the dental deposit.

The foregoing and other objects of this invention are attained by providing a drug for treating dental caries, comprising an active principle and a pharmaceutical diluent, and characterized, according to the invention, in that the active principle is a mixture of sodium monofluorophosphate and an anticarious composition obtained by treating osseous tissue with a diluted mineral acid till a complete dissolution of mineral components and water-soluble proteins contained in the osseous tissue, separating the solution, diluting it with water, adding a stabilizer, i.e., citric acid or its salt, to the solution, and neitralizing and evaporating the solution, which anticarious composition has the following percentage-by-weight composition:

| | |
|---|---|
| calcium | 2-6 |
| sodium | 19-23 |
| potassium | 0.04-0.18 |
| mineral acid anions | 6-10.6 |
| orthophosphoric acid anions | 1.5-5.0 |
| water-soluble proteins | 1.0-5.0 |
| magnesium | 0.05-0.2 |
| trace elements, including fluorine, manganese, tin, zinc, and iron | 0.01-0.02 |
| complex citrate compounds in terms of citric acid anions | the balance; | the ratio between the active principle and pharmaceutical diluent being 1:23.5-24.5.

The drug of this invention is intended for peroral administration in the form of tablets. One tablet preferably contains the following amount of the active principle:

| | |
|---|---|
| sodium monofluorophosphate | 0.0065-0.0075 g |
| anticarious composition | 0.16-0.18 g |

The pharmaceutical filler is preferably starch or lactose.

DETAILED DESCRIPTION OF THE INVENTION

As pointed out above, the drug of this invention is administered in the form of tablets or pills.

The tablets are white, odorless and of a sweetish taste. They are well soluble in water and saliva. A tablet should be chewed before swallowing. Chewing a tablet during 2 to 3 minutes produces a local therapeutical effect. When swallowed, a tablet produces a general therapeutical effect, raising the resistance to caries of hard and soft tissues in the oral cavity and reducing the cariesogenic action of the dental deposit. Compare the effects of the proposed anticarious drug with those of Calcipot-F. In the case of the former, the increase in the concentration of fluorine ions is 6 to 7 times, of calcium ions 2 to 2.5 times, and of phosphorus ions 2 times as high as in the case of Calcipot-F. The anticarious action the novel drug is twice as effective as that of Calcipot-F. Following a course of treatment with the novel drug, the permeability of the dental enamel is three times lower, and the dental deposit is twice less cariesogenic than after a course of treatment with Calcipot-F. The anticarious drug of this invention and its active principle have undergone laboratory tests on animals and clinical tests on humans.

The series of laboratory experiments included tests of 3% solution of the anticarious composition contained in the drug according to the invention. The experiments were performed on 80 one month old Wistar rats of which 40 made up the control group. All the animals were put on the Stephan-580 cariesogenic diet. 3% solution of the anticarious composition was applied to the teeth of the test animals during 3 minutes every day over a period of four weeks. Teeth were then extracted and the cariosity index was determined by using conventional techniques. The results of the experiments are listed in Table 1.

TABLE 1

Anticarious Effects of 3% Solution of Anticarious Compound in Accordance with the Invention

| | | Indices | | | | | |
|---|---|---|---|---|---|---|---|
| | | Fissure zones | | Contact zones | | All zones | |
| Nos. | Group | Cariosity index | Anticarious action, % | Cariosity index | Anticarious action, % | Cariosity index | Anticarious action, % |
| 1 | 2 | 3 | 4 | 5 | 6 | 7 | 8 |
| 2 | Control group | 26.75 | — | 2.76 | — | 29.51 | — |
| 3 | Test group | 20.42 | 23.7 | 1.00 | 63.7 | 21.42 | 27.4 |

3% solution of the anticarious compound according to the invention was administered to children 7 to 10 years old once every two weeks over a period of no less than 18 months. The increase in the DMF-T index was slowed down to 44.1-53.7 percent, and in the DMF-S index to 40.2-58.0 percent. CRT tests showed a marked improvement in the acid resistance of the enamel.

3% solution of the anticarious compound according to the invention is highly effective in the treatment of dental caries at its early stages. Demineralization spots were eliminated or reduced in 72.4 to 84.0 percent of cases. Cariosity was arrested in 14.0 to 31.9 percent of cases. The absence of curative action was observed in 2 to 8 percent of cases.

3% solution of the anticarious compound according to invention is quite effective in treating hyperesthesia of hard dental tissue. Abnormal sensitivity of the dental neck is eliminated in 23.2 to 36.4 percent of cases.

Clinical tests of the anticarious compound of this invention were carried out with a view to investigating its caries prevention effects in children and expectant mothers and its effectiveness in the conservative treatment of focal demineralization of dental enamel. 1.5-3% solutions of the anticarious compound were used for the purpose.

Following an epidemiological investigation, 176 children 6 to 7 years old were selected. Solution of the anticarious compound according to the invention was administered in the form of applications to 81 children. The remaining 95 children made up the control group.

Solution was applied after a child had brushed his or her teeth with tooth paste. The teeth were then protected from saliva by lignin and dried by a flow of air. The solution was applied to the entire surface of the teeth with the aid of spoons of an elastic material, such as plastic, carrying loose cotton tampons previously dipped into the solution. The tampons were allowed to remain on each jaw for 10 minutes. After the seance of treatment the children were told to abstain from food and drink for two hours. They were thus treated once every two weeks.

The initial oral cavity examination had revealed a relatively uniform cariosity level of $1.12\pm0.13$ to $1.30\pm0.13$ according to DMF-T.

The results of the experiments are shown in Table 2.

The table indicates that the caries growth was reduced to 44.7% and 49.5% for DMF-T and DMF-S, respectively.

As regards the effects of the compound under investigation on isolated groups of teeth, it was established that its application was beneficial both to the first molars and to the incisors that had erupted during the observation period.

Solution of the anticarious compound according to the invention was used to treat dental demineralization in 81 children aged 7 to 14.

The children were divided into two groups. The first included 42 children with slowly progressing demineralization. The second included 39 children with rapidly progressing demineralization. These groups were designated 3a and 3b, respectively.

Demineralization was observed on 229 teeth in Group 3a and on 248 teeth in Group 3b (Table 3). The groups described in connection with the previous experiment were designated 1a and 1b and used as control groups.

10 to 15 applications had to be made in Group 3a, and 20 to 25 in Group 3b to attain a positive result.

Remineralization therapy was more effective in the case of slowly progressing demineralization. Spots with an area of 2 $mm^2$ and 2 to 3 $mm^2$ disappeared or diminished faster than larger spots. Conservative treatment of rapidly progressing dental demineralization in children of Group 3b was less effective, but the relationship the spot size and the effectiveness of treatment was the same (Table 4).

In Group 3a, spots were fully eliminated on 193 teeth out of 229 (84%$\pm$2.4), as compared with the control group where the same applies only to 100 teeth out of 270 (36%$\pm$2.9).

TABLE 2

Dynamics of Dental Caries

| | | | | Observations after 1 year | | | |
|---|---|---|---|---|---|---|---|
| | | | Number | Caries Growth | | Reduction of growth, % | |
| Nos | Group | Type of treatment | of cases | DMF-T | DMF-S | DMF-T | DMF-S |
| 1 | 2 | 3 | 4 | 5 | 6 | 7 | 8 |
| 2 | I | Applications of remineralizing solution | 81 | $0.78 \pm 0.16$ | $1.12 \pm 0.28$ | 19.6 | 22.7 |
| 3 | II | Control | 95 | $0.97 \pm 0.14$ | $1.45 \pm 0.24$ | — | — |

| | | | Observations after 3 years | |
|---|---|---|---|---|
| | | | Number | Reduction of |

TABLE 2-continued

| | | Dynamics of Dental Caries | | | |
|---|---|---|---|---|---|
| | of | Caries Growth | | growth, % | |
| Nos | cases | DMF-T | DMF-S | DMF-T | DMF-S |
| 1 | 9 | 10 | 11 | 12 | 13 |
| 2 | 81 | 1.61 ± 0.18 | 2.59 ± 0.34 | 44.7 | 49.5 |
| 3 | 78 | 2.91 ± 0.16 | 5.13 ± 0.25 | — | — |

Cariosity were discontinued in 31 teeth in Group 3a (14%±6.23) and in 87 teeth in the control group (31%±2.8).

In Group 3a, an increase in the size of the spots and cavitation were only observed on 5 teeth out of 229 (2%±0.9), whereas in the control group the same phenomena were manifest on 92 teeth out of 279 (33%±2.8).

The different results obtained in Test Group 3a and Control Group 1a are statistically trustworthy (Table 4).

In Group 3b, treatment of rapidly progressing demineralization was successful on 155 teeth out of 248 (63%±3.0), whereas in the control group a spontaneous disappearance of demineralization spots was only observed on 33 teeth out of 305, which is a mere 11%±4.8. In Group 3b, cariosity was stopped on 60 teeth (24%±2.7), although at the same time demineralization spots developed into cavities on 33 teeth (13%±2.1).

TABLE 3

| | | Spot Size Distribution | | | |
|---|---|---|---|---|---|
| | | Number of Teeth with Demineralization Spots | | | |
| Nos | Spot Size | Group 1a (control) | Group 1b (control) | Group 3a | Group 3b |
| 1 | 2 | 3 | 4 | 5 | 6 |
| 2 | 2 mm² | 73 | 48 | 81 | 24 |
| 3 | 2-3 mm² | 125 | 102 | 117 | 120 |
| 4 | 3 mm² | 81 | 155 | 31 | 104 |
| 5 | Total number of spots | 279 | 305 | 229 | 248 |

The different results obtained in Test Group 3b and Control Group 1b are statistically trustworthy (Table 4).

To summarize, the use of the anticarious compound of this invention for treatment of slowly or rapidly progressing demineralization of dental enamel produces positive results in 73.5 percent of cases.

Solution of the anticarious compound was also tested on expectant mothers. According to epidemiological studies, cases of demineralization of dental enamel becomes more frequent and demineralization grows more intense toward the end of pregnancy. A test group of 69 expectant mothers, referred to as Group 1, was selected to study the preventive action of the anticarious compound of this invention. The compound was used in the form of applications. 64 pregnant women were included in the control group, referred to as Group 2. The duration of pregnancy in both groups was 4 to 12 weeks.

A preliminary examination revealed more or less equal spot demineralization levels of 29 to 30 percent in both groups. The average number of damaged teeth was 1.8±0.3.

By the end of the pregnancy period, the incidence of demineralization had gone up to 64% in the control group, and the average number of damaged teeth was 5.23±0.7.

In group 1, the anticarious compound according to the invention prevented the development of new foci of demineralization and stopped the spread of the old ones: their size remained the same, and they had not developed into cavities.

The anticarious drug of this invention was prepared in the form of tablets and thus tested for its effect on the basic functions of animal organisms in acute and chronic experiments. Acute experiments were performed on white mice and rats. Chronic experiments were performed on rats, guinea pigs, and puppies. Thus the experiments involved a total of four animal species. Different experimental techniques were used, and toxicological, biochemical and histological investigations carried out to ascertain the non-toxic nature of the drug in accordance with the invention.

Acute toxicity of 30% aqueous suspension of the anticarious compound according to the invention was studied on white mice of both sexes weighing 15 to 31 g. The compound was administered per os with the aid of a metal probe in an amount of 6,000 mg/kg, 8,000 mg/kg, 13,000 mg/kg, 14,000 mg/kg, 15,000 ,g/kg, and 16,000 mg/kg. A higher dose would have meant exceeding the maximum amount of suspension that could be administered. The animals were under observation for 10 days after the administration of the anticarious compound. During that period they were all given their habitual rations.

TABLE 4

| | Results of Treating Children with Remineralizing Solution of Anticarious Compound According to Invention | | | | | | |
|---|---|---|---|---|---|---|---|
| | Result of Treatment for Demineraliza- tion of Dental | Characteristics of Demineralizations Spots Spot Distribution in Group 3a | | | | | t in comparison with control |
| | | Size | | | Quantity | | |
| Nos. | Enamel | 2 mm² | 2-3 mm² | >3 mm² | Abs. | M ± m, % | (p < 0.001) |
| 1 | 2 | 3 | 4 | 5 | 6 | 7 | 8 |
| 2 | Disappearance of spots | 64 | 98 | 31 | 193 | 84 ± 2.4 | 10.8 |
| 3 | Discontinuation of | 13 | 18 | — | 31 | 14 ± 2.3 | 4.5 |

TABLE 4-continued

Results of Treating Children with Remineralizing Solution of Anticarious Compound According to Invention

| | process | | | | | | |
|---|---|---|---|---|---|---|---|
| 4 | Formation of defects | 4 | 1 | — | 5 | 2 ± 0.9 | 8.9 |
| 5 | Total: | | | | 229 | 100 | |

| | Characteristics of Demineralizations Spots Spot Distribution in Group 3b | | | | | |
|---|---|---|---|---|---|---|
| | Size | | | Quantity | | t in comparison with control |
| Nos | 2 mm² | 2-3 mm² | >3 mm² | Abs. | M ± m, % | (p < 0.001) |
| 1 | 9 | 10 | 11 | 12 | 13 | 14 |
| 2 | 19 | 73 | 63 | 155 | 63 ± 3.0 | 12.8 |
| 3 | 1 | 31 | 23 | 60 | 24 ± 2.7 | 3.4 |
| 4 | 4 | 16 | 13 | 33 | 13 ± 2.1 | 14.7 |
| 5 | | | | 248 | 100 | |

$LD_{50}$ level could not be established, because even the maximum possible doses did not kill any of the animals. Following an administration of the anticarious compound in an amount of 16,000 mg/kg, tremor and temporary paralysis of hind legs were observed during five minutes in two mice out of the total of six subjected to the experiment. Lower doses did not change the behaviour of the animals.

The experiments point to a low toxicity level of the anticarious compound according to the invention in the form of tablets administered per os.

Acute toxicity of the anticarious compound was studied on rats of both sexes weighing 90 to 110 g. The compound was administered in the form of 30% aqueous suspension in an amount of 14,500 mg/kg and 16,000 mg/kg, whereafter the animals were under observation for 10 days. During that period they were on their ordinary diet. Not a single fatal outcome was registered. During the first 2 to 3 hours the animals looked weary and sluggish. The $LD_{50}$ level could not be established, because the maximum dose not kill any of the animals.

The inference is low toxicity of the anticarious compound according to the invention if it is administered per os.

Chronic toxicity of the compound was studied on young guinea pigs, rats, and puppies. The compound in no way affected the general state and growth of the animals. Hematologic investigation (namely, the establishment of the number of erythrocites and leucocytes, the hemoglobin level, the erythrocyte sedimentation rate, and the differential blood count) and a biochemical analysis of blood and urea of the test animals did not reveal any pathological changes. Prolonged peroral administration of the anticarious compound according to the invention did not affect the cardiovascular system, endocrine system, and hemopoietic organs. No pathological changes were observed in the organs of the sacrificed animals. It is equally important that the anticarious compound of this invention involves no irritation or allergy hazards.

The effects of the anticarious compound of this invention on humans were compared to those of Calcipot-F.

The dynamics of the transition of the active ingredients of tablets to saliva were studied by analyzing the saliva of 20 stomatologic school students immediately after they had chewed tablets of Calcipot-F and those of the anticarious compound in accordance with the invention. The ionized and hydrolyzable fluorine content was determined electrochemically through the use of fluorine-selective electrodes. The phosphorus content was determined with the aid of spectrophotometry. The Ca content was determined by using the atomic absorption techiques.

The effects of the above-mentioned anticarious drugs on the permeability of dental enamel with regard to $Ca^{45}$ were studied on 24 fangs of six dogs 2 to 4 years of age following a single 30-minute application of electuary prepared from both drugs. The percentage of permeability was calculated with reference to the control, i.e., fangs to which no drug was applied.

The anticarious action of the two drugs, the rate of transition of fluorine compounds to the surface layers of the dental enamel and the acid resistance of the enamel were studied on 75 four-week old Wister rats. The two test groups consisted on 25 animals each. The remaining 25 animals made up the control group. All the animals were put on the Stephan-580 cariesogenic diet for four weeks. Suspension of Calcipot-F and suspension of the anticarious compound of this invention was applied for 60 to 90 seconds to the teeth of the first and second test groups, respectively. The application was done with the aid of a small brush. At the end of the experiment the teeth were extracted and the cariosity index was determined by using conventional techniques. Following biopsy, the fluorine content in the surface layer of the enamel was determined electro-chemically.

The acid resistance of the enamel (the CRT test) was evaluated by using the Muhlemann and Wolgensinger method (cf. Muhlemann, Wolgensinger, Helv. odonf., Acta, 1959, 3, 35-38) on 150 upper incisors of rats whose molars were used to study the anticarious effects of Calcipot-F and the drug of this invention, as well as the transition of fluorine to the dental enamel.

The cariesogenic action of the dental deposit was studied on 45 persons who had volunteered for the experiment. 30 of them were divided into two test groups of 15. The experiments were based on the Hardwick method (cf. Hardwick, Brit. dent., 1960, 108, 255-260). Prior to the experiment, the subjects were told not to brush their teeth for 24 hours. The control group consisted of 15 persons.

The inhibition of the acid-producing microflora of the dental deposit was studied on the same 45 volunteers who took tablets of Calcipot-F and those of the anticarious compound according to the invention. The tablets were thoroughly chewed. Appropriately dosed samples of dental deposit were analyzed as they were successively diluted in physiological solution. Tolerant and elective liquid and agarized nutrient media were used for the vegetation of streptococci and lactobacteria isolated from dental deposit samples. Quantitative evaluation was done on the basis of titers of microorganisms.

30 patients with similar manifestations of gingivitis at its initial stage were selected as subjects with a view to determining the opsono-phagocytic index and the lisozyme content in the saliva and comparing the antiinflammatory action of Calcipot-F and of the anticarious compound according to the invention. Some patients took tablets of the former, while others took tablets of the latter. The antiinflammatory action was evaluated by using the conventional procedure. Autostrains of Staphlococcus aureus isolated from the contents of the groove between the gum and the teeth were used as the test culture. The total number of phagocytized microorganisms per smear was counted and the arithmetic mean per leucocyte was calculated and taken as the opsonophagocytic index. The activity of lisozyme is indicative of the state of the local protection factors. This activity was determined in mixed saliva 90 to 120 minutes after breakfast by radial diffusion in biphthalate agar. The lisozyme level was expressed in micrograms per milliliter. The results of the tests are presented in Tables 5 and 6.

TABLE 5

Transition of Active Ingredients of Tablets to Saliva

| Anticarious drug | Saliva composition, mg/l | | | |
|---|---|---|---|---|
| | Ionized fluorine | Hydrolyzable fluorine | Ca | P |
| Control (no drug used) | 0.03 | — | 65 | 207 |
| Tablets of Calcipot - F | 4.5 | 0.4 | 304 | 217 |
| Tablets of anticarious compound according to invention | 26.2 | 39.1 | 794 | 452 |

TABLE 6

Comparison of Characteristics of Calcipot - F and Anticarious Compound According to Invention

| Nos 1 | Anticarious drug 2 | Permeability of dental enamel to $Ca^{45}$, % of control 3 | Anticarious action, % 4 | F content in surface layer of enamel, wt. % 5 | Acid resistance of dental enamel in rats (CRT test), sec 6 |
|---|---|---|---|---|---|
| 2 | Control (no drug used) | 100% | 0 | 0.074 ± 0.0009 | 28.4 ± 7.7 |
| 3 | Tablets of Calcipot - F | 84.8 | 12.4 | 0.0099 ± 0.0008 | 35.2 ± 3.1 |
| 4 | Tablets of anticarious compound according to invention | 59.7 | 35.2 | 0.0248 ± 0.0009 | 65.5 ± 1.8 |

| Nos 1 | Cariesogenic action of dental deposit in man 7 | Number of acid-producing micro-organisms in dental deposite of man in titers 8 | Opsophago-cytic index of human saliva, units 9 | Lisozyme content in saliva, mkg/ml 10 |
|---|---|---|---|---|
| 2 | ++++ | Streptococci: $10^{-6}-10^{-7}$ Lactobacteria: $10^{-5}-10^{-6}$ | 2.5–3.0 | 190–195 |
| 3 | ++ | Streptococci: $10^{-4}$ Lacto-bacteria: $10^5$ | 1.9–2.2 | 180–186 |
| 4 | 0+ | Streptococci: $10^{-2}-10^{-3}$ Lactobacteria: $10^{-3}-10^{-4}$ | 1.1–1.4 | 180–195 |

An analysis of the above data indicates that in the case of the anticarious compound according to the invention the concentration of the active ingredients, namely, fluorine compounds and phosphorus-calcium salts, in the oral cavity is 2 to 7 times higher than in the case of Calcipot-F. When a tablet of the anticarious compound of this invention is taken by a patient, the permeability of the dental enamel to $Ca^{45}$ decreases by about 30 percent, which prevents penetration of harmful agents from the saliva to the hard tissue of the teeth. The anticarious effect of the compound of this invention is 3 times stronger than that of Calcipot-F. In the case of the compound of this invention the penetration of its active ingredients, especially fluorine, to the dental tissue is 2.5 times more intense and the acid resistance of the dental enamel is higher by 80 percent than in the case of Calcipot-F. The cariesogenic action of the dental deposit is reduced to a minimum due to lower titers of the acid-producing microflora. In patients taking tablets of the anticarious compound according to the invention, the opsono-phagocytic index is close to the normal physiological level. At the same time the compound according to the invention does not affect the natural protection factors, as indicated by a high content of lisozyme in the saliva.

The anticarious drug of this invention can be tabletted in the conventional manner.

The anticarious compound contained in the drug is produced as follows. A mineral acid is poured over osseous tissue. The tissue is allowed to dissolve in the mineral acid and the solution is stirred to effect a complete dissolution of the mineral components and water-soluble proteins contained in the osseous tissue.

The solution is separated and diluted with water. Citric acid or its salt are added to the solution, whereupon it is neutralized.

The solution is then sprayed in a drying chamber so as to obtain a dry product convenient for storage and transportation.

This product is a white amorphous odorless powder of a saltish taste. It is readily soluble in water, poorly soluble in 95% alcohol, and almost insoluble in ether.

The daily dose, in grams, of the compound is as follows: sodium monofluorophosphate, 0.0065–0.0075; the anticarious compound according to the invention, 0.16–0.18. The anticarious drug is taken daily during 250 days. The tablets should be chewed before swallowed. The anticarious drug of this invention produces no side effects. There are no contraindications to its use.

What is claimed is:

1. A drug for treatment of dental caries, comprising an active principle, namely, a mixture of sodium monofluorophosphate and an anticaries composition obtained by treating osseous tissue with a diluted mineral acid till a complete dissolution of the mineral components and water-soluble proteins contained in the osseous tissue, separating the solution, diluting it with water, adding as a stabilizer, citric acid or its salt, to the solution, and neutralizing and evaporating the solution, which anticaries composition has the following percentage-by-weight composition:

| | |
|---|---|
| calcium | 2–6 |
| sodium | 19–23 |
| potassium | 0.04–0.18 |
| mineral acid anions | 6–10.6 |
| orthophosphoric acid anions | 1.5–5.0 |
| water-soluble proteins | 1.0–5.0 |
| magnesium | 0.05–0.2 |
| trace elements, including fluorine, manganese, tin, zinc, and iron | 0.01–0.02 |
| complex citrate compounds in terms of citric acid anions | the balance; | and a chewable and swallowable water and saliva-soluble pharmaceutical diluent, the ratio between said active principle and said pharmaceutical diluent being 1:23.5–24.5.

2. A drug as claimed in claim 1 in the form of chewable and swallowable tablets, each tablet containing the following amount of the active principle:

| | |
|---|---|
| sodium monofluorophosphate | 0.0065–0.0075 g |
| anticaries composition | 0.16–0.18 g. |

3. A drug as claimed in claim 1 in the form of tablets, wherein the pharmaceutical diluent is a filler selected from the group consisting of starch and lactose.

* * * * *

UNITED STATES PATENT AND TRADEMARK OFFICE
CERTIFICATE OF CORRECTION

PATENT NO. : 4,419,341

DATED : December 6, 1983

INVENTOR(S) : Anatoly G. Kolesnik, et al

It is certified that error appears in the above-identified patent and that said Letters Patent is hereby corrected as shown below:

In column 1 of the title page, the names of the first two inventors are not set out.

The names of the first two inventors should be set out, as follows:
Gennady N. Pakhomov, Moscow and
Anita Y. Luste, Riga On the title page after United States Patent (19), "Kolesnik et al". should read -- Pakhomov et al. --.

Signed and Sealed this

Twenty-fourth Day of April 1984

[SEAL]

Attest:

GERALD J. MOSSINGHOFF

Attesting Officer

Commissioner of Patents and Trademarks